United States Patent [19]

Lenfant et al.

[11] Patent Number: 5,112,811
[45] Date of Patent: May 12, 1992

[54] SDK PEPTIDES AND THERAPEUTIC COMPOSITIONS CONTAINING THEM

[75] Inventors: Maryse Lenfant; Josiane Thierry, both of Yvette, France

[73] Assignee: Societe de Conseils de Recherches et d'Applications Scientifiques, Paris, France

[21] Appl. No.: 489,449

[22] Filed: Mar. 6, 1990

[30] Foreign Application Priority Data

Mar. 11, 1989 [GB] United Kingdom ............... 8905606

[51] Int. Cl.$^5$ .................. C07K 5/08; C07K 5/10; C07K 7/06
[52] U.S. Cl. ...................... 514/17; 514/18; 530/330; 530/331
[58] Field of Search ............... 530/330, 331; 514/17, 514/18

[56] References Cited

U.S. PATENT DOCUMENTS

| | | | |
|---|---|---|---|
| 4,161,522 | 7/1979 | Hamburger | 530/330 |
| 4,816,449 | 3/1989 | Hahn | 530/330 |
| 4,851,509 | 7/1989 | Jolles et al. | 530/330 |
| 4,933,323 | 6/1990 | Noguchi et al. | 530/330 |
| 4,943,562 | 7/1990 | Jolles et al. | 530/330 |

Primary Examiner—Lester L. Lee
Attorney, Agent, or Firm—Lucas & Just

[57] ABSTRACT

The invention relates to peptides having the general formula

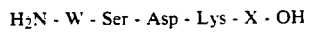

$H_2N$ - W - Ser - Asp - Lys - X - OH wherein X represents a Pro or Lys residue or a valence bond and W represents a Thr or Pro residue or a valence bond with the proviso that if X represents a Pro residue then W also represents a Pro residue; to a process for the preparation of the same and to therapeutic compositions containing said peptides.

11 Claims, No Drawings

SDK PEPTIDES AND THERAPEUTIC COMPOSITIONS CONTAINING THEM

The present invention relates to SDK peptides, to a preparation process of the same and to therapeutic compositions containing them.

The abbreviations used in this Specification follow the 1983 Recommendations on Nomenclature on Symbolism for Amino Acids Peptides of the IUPAC-IUB Joint Commission on Biochemical Nomenclature (Eur. J. Biochem. 138, 9–37 (1984)). For ease of understanding, however, certain of these abbreviations are set out below:

Asp or D: aspartic acid
Ser or S: serine
Lys or K: lysine
Pro or P: proline
Thr or T: threonine
Z: benzyloxycarbonyl
Boc: t-butoxycarbonyl
OBzl: benzyloxy
Ac: acetyl
Other abbreviations used include:
DMF: dimethylformamide
DCM: dichloromethane
NMM: N-methylmorpholine
TFA: trifluoroacetic acid
TLC: thin layer chromatography
FAB: fast atom bombardment The invention relates to peptides having the general formula I

$H_2N$ - W - Ser - Asp - Lys - X - OH     1 wherein X represents a Pro or Lys residue or a valence bond; and W represents a Thr or Pro residue or a valence bond; with the proviso that if X represents a Pro residue then W also represents a Pro residue.

The peptides included within the general formula I may be listed as follows:

| | |
|---|---|
| Ser-Asp-Lys | (i) |
| Ser-Asp-Lys-Lys | (ii) |
| Pro-Ser-Asp-Lys-Lys | (iii) |
| Thr-Ser-Asp-Lys-Lys | (iv) |
| Pro-Ser-Asp-Lys | (v) |
| Thr-Ser-Asp-Lys | (vi) |
| Pro-Ser-Asp-Lys-Pro | (vii) |

The invention includes pharmaceutically acceptable salts of the peptides of the general formula I.

This tripeptide (i), on which the other peptides of the invention are based, does not appear to have been isolated or prepared to date. However, these sequences of amino-acids have been found in various living proteins, for example Ser-Asp-Lys in lymphocyte T membrane protein, where its action appears when a portion of a lymphocyte marker such as lymphocyte $CD_2$ as well as an α- or a γ-subunit of a T-receptor, which comprise the specific sequence which takes a position in regard of certain specific receptors of the lymphocyte these amino-acid sequences may be also found in various proteins such as proteins of viruses and also in certain proteins of the complement or tumour necrosis factor α.

Accordingly, it was particularly interesting to investigate the activity of the specific amino-acid sequences and, according to the invention, it has been found that they play active roles in the field of immuno-modulation as evidenced by the immunologic reports.

This invention also relates to a preparation process of these peptides conducted by usual routes through the following reaction sequence:

K(Z) - X(10) - OH     I

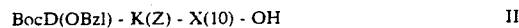
BocD(OBzl) - K(Z) - X(10) - OH     II

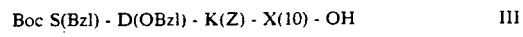
Boc S(Bzl) - D(OBzl) - K(Z) - X(10) - OH     III

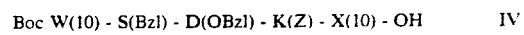
Boc W(10) - S(Bzl) - D(OBzl) - K(Z) - X(10) - OH     IV with the conventions that:
a) the brackets following W or X are void when W and X stand for Pro, the brackets following W contain Bzl when W stands for Thr and the brackets following X contain Z when X stands for Lys, and
b) when W and/or X stand for a valence bond, the corresponding step is omitted.

When a therapeutically acceptable salt is prepared, e.g. acetyl, the salification should be conducted before the final deprotection step.

The solvents herewith used are of Purex quality. DMF is stored on 3 and 4 Å-molecular sieve.

TLCs are run on commercial analytic plates. Plates have been observed at 254 nm and revealed with a ninhydrine solution and according to Pataki. The following solvents are used:

A: DCM/methanol (8/2 by volume)
B: n-butanol/AcOH/water (4/1/1 by volume) and
C: n-butanol/AcOH/water/pyridine (1/1/1/1 by volume).

Intermediate products are purified on a silica column when necessary (silica 60 Å(40-60 μ) SDS), they are characterized by their mass spectrum (molecular peak or $MH^{30}$), and by fast atom bombardment (FAB).

Final products are purified by HPLC with a semi-preparative column (7.2 mm×250 mm) $C_{18}ODS$ Hypersil 10 μ SFCC, with isocratic mode or with gradient.

Analysis of amino-acids are carried out after acid hydrolysis of the peptide with 6N HCl, at 110° C. for 12 hours on an HPLC apparatus.

This invention relates, finally, to therapeutic compositions of matter, the active ingredient therein being a sufficient amount of the said peptides associated with carriers suitable for the selected administration route.

The invention will be better understood from the description of the preparation of Ser-Asp-Lys (i).

Synthesis of Peptides

Syntheses have been carried out step by step with the mixed anhydride method, using isobutyl chloroformate or by the active esters method, using the esters of N-hydroxy-succinimide. Protected amino-acids are commercial ones.

Deprotection

The Boc group is cleaved by acidolysis using TFA: the peptide is treated with a mixture (1/1 by volume) of DCM/TFA (10 to 30 equivalents) for 1 to 2 hours, at room temperature.

The ZBzl or OBzl groups are hydrogenolysed. The peptide, in solution in a mixture of methanol/water (9/1 by volume), is hydrogenolysed in presence of Pd/C at 10%.

Acetylation

Acetylation is carried out by reacting acetylimidazole on the trifluoroacetate of the amine neutralized by triethylamine in DMF.

Preparation of Boc D(OBzl) K(z) 1

The ester of the N-hydroxysuccinimide of Boc D(OBzl) (1 mole) is dissolved in 2.5 ml of DMF. K(Z) (1.1 eq.) in suspension is added to this solution, put on an ice-bath and 1.1 eq. of triethylamine is added under stirring. Stirring is maintained for 24 hours. The reaction mixture is evaporated under reduced pressure. The residue is then treated with ethyl acetate and a solution of 0.5 N HCl. The organic phase is washed with water, then with a saturated solution of sodium chloride, dried on sodium sulphate and finally evaporated under reduced pressure. The residue is chromatographed on a silica gel column and eluted with a mixture of DCM/methanol (95/5 by volume). The homogeneous fractions from TLC are collected. Yield : 0.540 g.

Preparation of Boc S(Bzl) D(OBzl) K(Z) 2

0.5 mM of 1 is treated with a mixture of 1.4 cm$^3$ of TFA/DCM (1/1 by volume) (20 equivalents). After 60 minutes at room temperature, the solvents are evaporated off under reduced pressure. The residue is treated twice with DCM and dried under reduced pressure in the presence of KOH.

The ester of the N-hydroxysuccinimide of Boc S(Bzl) (1.2 eq.) and the trifluoroacetate previously obtained are dissolved in 1.3 ml of DMF. One equivalent of triethylamine is added under magnetic stirring. The stirring is maintained for 24 hours. The reaction mixture is treated as for 1. The residue is chromatographed on silica gel and the resulting product is eluted with a mixture of diethylether/ methanol (8/2 by volume). The homogeneous fractions from TLC are collected (yield : 0.318 g, 83 %). When triturating with pentane, a solid is obtained (0.27 g). Mass Spectrometry (MS) (FAB) MH+, 763 were calculated ; 763 and 763.100 were found (MH+- Boc).

Preparation of NAc S(Bzl) D(OBzl) K(Z) 3

The derivative 2 is deprotected by a solution 3.1N HCl (20 equivalents) in tetrahydrofuran. The solution is stirred at room temperature for 6 ½ hours. The reaction mixture is evaporated and dried under reduced pressure for one night in the presence of KOH.

The resulting chlorhydrate and 1.1 equivalent of acetylimidazole are dissolved in 1 ml of DMF. The pH of this solution is brought to 7.5 with triethylamine. The mixture is stirred for 22 hours. The reaction mixture is then evaporated and the residue treated by ethyl acetate and a 0.5N solution of HCl. The organic phase is washed with water and a saturated solution of sodium chloride and then dried on sodium sulphate. MS FAB MH+, 705 were calculated and 705 observed.

Preparation of NAc SDK 4

0.140 g of 3 (0.2 mM) dissolved in 3 ml of methanol and 1 ml of water are hydrogenolysed for 22 hours in the presence of 10% Pd/C. The catalyst is filtered off on a celite pad and the solvent evaporated off under reduced pressure. Yield : 0.079 g. TLC shows 2 spots sensitive to ninhydrine.

The product is purified by HPLC, isocratic mode ; eluent : water : TFA 0.1 % ; flow rate 4 ml/min ; t =8 min.

Analysis of amino-acids : S : 0.9 (1) ; D : 1.3 (1) ; K : 1.3 (1)

MS : FAB MH+391 were calculated and 391 observed.

Preparation of SDK 5

The tripeptide 2 is initially treated with a mixture of TFA/DCM (1:1 by volume) for one hour and a half the solvents are then evaporated off under reduced pressure and the residue treated with toluene ; the solvent is evaporated off and the residue is hydrogenolysed in a solution of 3 ml of methanol and 0.3 ml of water for 20 hours at room temperature and in the presence of 0.030 g of Pd/C. The catalyst is filtered on a celite pad and the solvent is evaporated off under reduced pressure. Yield : 0.090 g.

MS MH+349 were observed and 349 calculated.

5 is purified by HPLC, isocratic mode eluent : water, TFA 0.10 %, flow rate 2 ml/min ; t =6 min.

Analysis of amino-acids : S : 1(1) ; D : 0.8(1) ; K : 1.3(1)

The other peptides of the invention are prepared by the same technique as SDK.

The interest of the present invention will be exemplified by the following immunologic reports.

Rosettes Protocol

I - Preparation of Sheep Red Blood Cells

Wash three times the red blood cells (RBC) in RPMI 1640 or RBS or Hanks +antibiotic drugs. Centrifuge for 7 minutes at 3000 rpm.

Put the cells sap in suspension. Count. Bring to $2.10^8$ RBC/ml in a solution of RPMI at 20 % of Foetal Calf Serum (FCS) (4 ml formerly adsorbed on 1 ml of RBC sap, 30 minutes on an ice-bath, then centrifuge for 7 minutes at 3000 rpm and recover in sterile conditions).

II - Preparation of Jurkat T Cells

Take an aliquot of Jurkat T cells in culture. Make a viability with Trypan blue.

Then take the volume of cells required for practical work. Wash the cells three times in RPMI 1640 or PBS or Hanks +antibiotic drugs. Centrifuge for 7 minutes at 900 rpm.

Put the cells sap in suspension. Count. Bring to $2.10^6$ Jurkat T cells/ml of solution of RPMI at 20 % of adsorbed FCS.

III - Preparation of the Peptide

Inhibiting solution =SDK ($2.10^{-7}$ mole).

Peptides to be evaluated are dissolved in RPMI 1640 at the appropriate concentration.

IV - Test

Place, in the tube, 200 μl of the inhibiting solution +100 μl of Jurkat T cells $2.10^6$ M in RMPI +FCS 20 % ; leave 10 minutes on an ice-bath. Add 100 1 RBC 2.10M in RPMI +FCS 20 %.

Centrifuge for 5 minutes at 500 rpm. Leave overnight at 4° C.

V - Counting of Rosettes

Set the microscope : ocular : ×6 objective : ×7

Put carefully back in suspension the cells by tapping. Let it rest for a while.

Add, in the tube, 30 μl of Toluidine blue 1 % (to dye the lymphocytes). Tap gently.

Read 3 Malassex hemocytometer per experimental point.

Results are reported in the following table.

| Peptide | % ROSETTES (% INHIBITION) | |
| --- | --- | --- |
|  | SDK | PSDKP |
| Control | 63 ± 4 | 59 ± 4 |
| $10^{-4}$M | 38 ± 3 (−40%)* | 37 ± 7 (−37%)** |
| $10^{-5}$M | 45 ± 4 (−28%)*** | 33 ± 3 (−44%)* |
| $10^{-6}$M | 50 ± 2 (−22%)*** | 27 ± 5 (−54%)* |
| $10^{-7}$M | 49 ± 2 (−22%)*** | 45 ± 6 (−24%)*** |
| $10^{-8}$M | 40 ± 2 (−36%)* | 48 ± 2 (−19%)*** |
| $10^{-9}$M | 43 ± 1 (−32%)* | 48 ± 4 (−19%)*** |
| $10^{-10}$M | 43 ± 3 (−32%)* | 52 ± 5 (NS) |
| $10^{-11}$M | 40 ± 1 (−36%)* |  |
| $10^{-12}$M | 44 ± 3 (−30%)* |  |
| $10^{-13}$M | 51 ± 7 (−19%)*** |  |
| $10^{-14}$M | 55 ± 2 (−14%)*** |  |
| $10^{-15}$M | 63 ± 4 (NS) |  |

( ) % Inhibition
*α < 0.001
**α < 0.01
***α < 0.05

Isolation of Human Peripheral Mononuclear Cells

I - Isolation of (nPMN)

Dilute blood at ½ in PBS.

On 15 ml of Ficoll-Hypaque, put 35 ml of dilute blood.

Centrifuge 30 minutes at 1800 rpm, at room temperature.

Take the ring corresponding to mononuclear cells (MNC) back with Pasteur pipette.

Wash twice in PBS (centrifuge for 10 minutes at 1800 rpm).

Bring to $2.10^6$ cells/ml with RPMI 1640 "complete" medium +10 % SVF.

II - Reactive Products

PHA-M : Reconstitute a 5 ml bottle lyophylized with 5 ml of "complete" medium. Solution of 100 %. Dilute to obtain a 0.4 % solution.

Peptides

SDK : Tube $10^6$ mole +4.35 ml "complete" medium. Solution 2.3 $10^{-4}$ M.

Then dilute successively 450 μl "medium" +50 μl of dilution.

III- Protocol

In 96-well sterilized boxes NUNC :

100 μl of MNC at $2.10^6$ cells / ml ($2.10^5$ cells)

50 μl of PHA 0.4 % (0.1 % final)

50 μl of medium

30 μl of peptide ($3.10^{-5}$ M)

Incubate for 3 days at 37° C. in air/CO* atmosphere 95/5. During the last 24 hours, make a puls of [$^3$H] Thymidine : 1 μci/well. Pick up the wells on filters and count with a counter.

Results are reported in the following table.

| | Stimulation of T lymphocytes proliferation by Ser—Asp—Lys (SDK) and Pro—Ser—Asp—Lys—Pro (PSDKP) | |
| --- | --- | --- |
| | DNA synthesis induced in MNC stimulated by 0.1% PHA | |
| PBL with 0.1% PHA | cpm × $10^3$/$2.10^5$ cells | % stimulation |
| Control (RPMI 1640) + Autologous RBC + SDK $3.10^{-5}$M | 35 ± 2 44 ± 5 56 ± 5 | +26%** +60%* |
| Control (RPMI 1640) + SDK $3.10^{-10}$M | 40 ± 3 52 ± 5 | +30%*** |
| Control (RPMI 1640) + PSDKP $3.10^{-5}$M | 38 ± 3 54 ± 4 | +42%*** |

*α < 0.001
**α < 0.02
***α < 0.01
MNC: Mononuclear Cell

Humoral Response 6-to-8 week old mice of B6D2F1 strain are sensitized, on day 0, with 0.2 ml of a sheep red blood cells suspension [$10^8$ cells ] in a saline solution of Hanks.

The Ser-Asp-Lys and the Pro-Ser-Asp-Lys-Pro peptides (3 μg/kg) were injected in solution physiological serum, by IP route, in 0.2 ml, at the appointed time.

On day +4, animals are killed and the number of B lymphocytes which secrete IgM immunoglobulines are counted by the hemolysis plaque technique (Jerne method).

8 mice / batch. 4 determinations / animal made test : 2 experiments / point.

Results are reported in the following table.

| Stimulation of the humoral response in mice to sheep red blood cells a T dependant antigen by Ser—Asp—Lys and Pro—Ser—Asp—Lys—Pro peptides (Number of P.F.C./$10^6$ cells) | | | |
| --- | --- | --- | --- |
| PERIOD OF INJECTION | SUBSTANCES INJECTED | | |
| | Saline | Ser—Asp—Lys | Pro—Ser—Asp—Lys—Prp |
| −24 h | 444 ± 44 | 644 ± 170 (+45)* | 630 ± 142 (+42)* |
| 0 h | 459 ± 103 | 903 ± 133 (+97)* | 915 ± 140 (+99)* |
| +24 h | 407 ± 66 | 459 ± 103 (NS) | 475 ± 82 (NS) |
| +48 h | 407 ± 66 | 673 ± 110 (+65)* | 589 ± 101 (+45)* |
| +72 h | 459 ± 103 | 1073 ± 348 | 543 ± 112 |

| PERIOD OF | SUBSTANCES INJECTED | | |
|---|---|---|---|
| INJECTION | Saline | Ser—Asp—Lys | Pro—Ser—Asp—Lys—Prp |
| | | (+134)* | (NS) |

Stimulation of the humoral response in mice to sheep red blood cells a T dependant antigen by Ser—Asp—Lys and Pro—Ser—Asp—Lys—Pro peptides (Number of P.F.C./$10^6$ cells)

*$\alpha < 0.001$
**$\alpha < 0.01$
( ) % stimulation
Peptides concentration: 3 µg/kg

Toxicity

No toxicity was noticed for any of the peptides according to the invention when administered per se, at the maximum administrable doses, to rats and mice. By the IP route, no death was noticed at 1 g/kg for the same animals.

Presentation - Posology

Only Ser-Asp-Lys peptides may be administered orally and reach their target without substantial degradation ; tablets and elation capsules are suitable with dosage units containing 10 mg of Ser-Asp-Lys. By this route, higher peptides need protected forms and higher unitary dosage (20 mg). Daily doses may be from 10 to 100 mg (SDK) or from 20 to 200 mg for higher peptides. By IP route, daily doses are from 1 to 10 mg for immediate action but sustained release forms (microcapsules, microsphere or the like) may contain up to 300 mg for long term release form.

We claim:

1. A peptide having the general formula

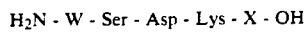

H₂N - W - Ser - Asp - Lys - X - OH wherein X represents a Pro or Lys residue or a valence bond ; and W represents a Thr or Pro residue or a valence bond ; with the proviso that if X represents a Pro residue then W also represents a Pro residue, and therapeutically acceptable salts thereof.

2. Ser-Asp-Lys.
3. Ser-Asp-Lys-Lys.
4. Pro-Ser-Asp-Lys-Lys.
5. Thr-Ser-Asp-Lys-Lys.
6. Pro-Ser-Asp-Lys.
7. Thr-Ser-Asp-Lys.
8. Pro-Ser-Asp-Lys-Pro.
9. A therapeutic composition of matter with immunomodulatory activity containing from 1 to 300 mg of a peptide according to claim 1, 2, 3, 4, 5, 6, 7 or 8 as an active ingredient associated with a pharmaceutically acceptable carrier for the selected administration route.
10. The composition of claim 9, for oral administration, which contains from 10 to 200 mg of active ingredient.
11. The composition of claim 9, for IP administration, which contains from 1 to 300 mg of active ingredient.

UNITED STATES PATENT AND TRADEMARK OFFICE
CERTIFICATE OF CORRECTION

PATENT NO. : 5,112,811
DATED : May 12, 1992
INVENTOR(S) : Maryse Lenfant et al.

It is certified that error appears in the above-identified patent and that said Letters Patent is hereby corrected as shown below:

Column 1, line 67, after "lymphocyte" insert --;--.

Column 2, lines 12-18, change the reaction sequence to read as follows:

--Boc K(Z) - X( ) - OH      I

Boc D(OBzl) - K(Z) - X( ) - OH      II

Boc S(Bzl) - D(OBzl) - K(Z) - X( ) - OH      III

Boc W( ) - S(Bzl) - D(OBzl) - K(Z) - X( ) - OH      IV--.

Column 2, line 43, change "$MH^{30}$" to --$MH^+$--.

Column 4, line 15, after "half" insert --;--.

Column 4, line 65, change "100 1 RBC 2.10M" to --100 µl RBC $2.10^8$M--.

Column 6, line 14, change "CO*" to --$CO_2$--.

UNITED STATES PATENT AND TRADEMARK OFFICE
CERTIFICATE OF CORRECTION

PATENT NO. : 5,112,811
DATED : May 12, 1992
INVENTOR(S) : Maryse Lenfant et al.

It is certified that error appears in the above-identified patent and that said Letters Patent is hereby corrected as shown below:

Column 6, lines 20-35, change the table to appear as follows:

--Stimulation of T lymphocytes proliferation by Ser-Asp-Lys (SDK) and Pro-Ser-Asp-Lys-Pro (PSDKP)

| PBL with 0.1% PHA | DNA synthesis induced in MNC stimulated by 0.1% PHA | |
|---|---|---|
| | cpm x $10^3/2.10^5$ cells | % stimulation |
| Control (RPMI 1640) | 35 ± 2 | |
| + Autologous RBC | 44 ± 5 | +26%** |
| + SDK $3.10^{-5}$M | 56 ± 5 | +60%* |
| Control (RPMI 1640) | 40 ± 3 | |
| + SDK $3.10^{-10}$M | 52 ± 5 | +30%*** |
| Control (RPMI 1640) | 38 ± 3 | |
| + PSDKP $3.10^{-5}$M | 54 ± 4 | +42%*** |

*$\alpha < 0.001$
**$\alpha < 0.02$
***$\alpha < 0.01$
MNC: Mononuclear Cell--.

UNITED STATES PATENT AND TRADEMARK OFFICE
CERTIFICATE OF CORRECTION

PATENT NO. : 5,112,811
DATED : May 12, 1992
INVENTOR(S) : Maryse Lenfant et al.

It is certified that error appears in the above-identified patent and that said Letters Patent is hereby corrected as shown below:

Column 6, line 43, after "solution" insert --in--.

Column 6, line 49, change "made" to --remade--.

Column 7, line 23, change "elation" to --gelatin--.

Signed and Sealed this

Twentieth Day of July, 1993

Attest:

MICHAEL K. KIRK

Attesting Officer     Acting Commissioner of Patents and Trademarks